United States Patent [19]

Luly et al.

[11] Patent Number: 4,645,759

[45] Date of Patent: Feb. 24, 1987

[54] RENIN INHIBITING COMPOUNDS

[75] Inventors: Jay R. Luly, Lake Bluff; John J. Plattner; Joseph F. Dellaria, both of Libertyville, all of Ill.

[73] Assignee: Abbott Laboratories, North Chicago, Ill.

[21] Appl. No.: 735,491

[22] Filed: May 17, 1985

Related U.S. Application Data

[63] Continuation-in-part of Ser. No. 623,807, Jun. 22, 1984, abandoned.

[51] Int. Cl.[4] .......................... A61K 37/43; C07K 5/08
[52] U.S. Cl. ...................................... 514/18; 530/331; 530/330
[58] Field of Search ................. 260/112.5 R; 530/330, 530/331; 514/18

[56] References Cited

U.S. PATENT DOCUMENTS 4,384,994  5/1983  Veber et al. ................. 260/112.5 R
4,424,207  1/1984  Szelke et al. ................. 260/112.5 R

FOREIGN PATENT DOCUMENTS 0045665  12/1982  European Pat. Off. .
0077028  4/1983  European Pat. Off. .

OTHER PUBLICATIONS

Kokubu et al., *Biochemical and Biophysical Research Communications*, 118, No. 3, 929–933, (1984).

Evin et al., *Proceedings in the Eights American Peptide Symposium*, 583–586, (1984).
Johnson et al., *J. Med. Chem.*, 23, 666–669, (1980).
Rudinger, *Peptide Hormones*, Parsons (ed.), U. Park Press, Baltimore, (1976), pp. 1–7.

*Primary Examiner*—Delbert R. Phillips
*Attorney, Agent, or Firm*—Steven F. Weinstock; Martin L. Katz

[57] ABSTRACT

The invention relates to renin inhibiting compounds of the formula

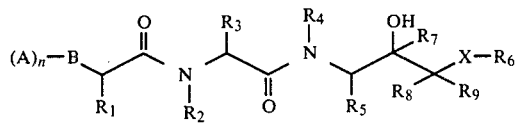

wherein A is an N-protecting group; n is 0 or 1; B is hydrogen, hydroxy, NH, loweralkyl or arylalkyl; with the proviso that when A is an N-protecting group, B is NH and when n is 0, B is hydrogen, hydroxy, loweralkyl or arylalkyl; $R_1$, $R_3$ and $R_5$ are loweralkyl or hydrophilic, lipophilic or aromatic amino acid side chains and may be the same or different; $R_2$, $R_4$, $R_7$, $R_8$ and $R_9$ are hydrogen or loweralkyl and may be the same or different; X is NH, O, S, SO or $SO_2$; and $R_6$ is loweralkyl, cycloalkyl, cycloalkylalkyl, aryl, arylalkyl or an N-protecting group, with the proviso that $R_6$ may be an N-protecting group when X is NH.

15 Claims, No Drawings

RENIN INHIBITING COMPOUNDS

TECHNICAL FIELD

This application is a continuation in part of U.S. application, Ser. No. 623,807 filed June 22, 1984, now abandoned.

The present invention relates to novel organic compounds which inhibit renin, processes for making such compounds, synthetic intermediates employed in these processes and methods of treating hypertension with such compounds.

BACKGROUND ART

Renin is a proteolytic enzyme synthesized and stored principally in a specific part of the kidney called the juxtaglomerular apparatus. Any of three different physiologic circumstances may cause the release of renin into the circulation: (a) a decrease in the blood pressure entering or within the kidney itself; (b) a decrease in the blood volume in the body; or (c) a fall in the concentration of sodium in the distal tubules of the kidney.

When renin is released into the blood from the kidney, the renin-angiotensin system is activated, leading to vasoconstriction and conservation of sodium, both of which result in increased blood pressure. The renin acts on a circulating protein, angiotensinogen, to cleave out a fragment called angiotensin I (AI). AI itself has only slight pharmacologic activity but, after additional cleavage by a second enzyme, angiotensin converting enzyme (ACE), forms the potent molecule angiotensin II (AII). The major pharmacological effects of AII are vasoconstriction and stimulation of the adrenal cortex to release aldosterone, a hormone which causes sodium retention. AII is cleaved by an aminopeptidase to form angiotensin III (AIII), which, compared to AII, is a less potent vasoconstrictor but a more potent inducer of aldosterone release.

Inhibitors of renin have been sought as agents for control of hypertension and as diagnostic agents for identification of cases of hypertension due to renin excess.

With these objectives in mind, the renin-angiotensin system has been modulated or manipulated, in the past, with ACE inhibitors. However, ACE acts on several substrates other than angiotensin I (AI), most notably the kinins which cause such undesirable side effects as pain, "leaky" capillaries, prostaglandin release and a variety of behavioral and neurologic effects. Further, ACE inhibition leads to the accumulation of AI. Although AI has much less vasocontrictor activity than AII, its presence may negate some of the hypotensive effects of the blockade of AII synthesis.

Inhibition of other targets in the renin-angiotensin system such as AII with compounds such as saralasin can block AII activity, but would leave unimpaired and perhaps enhance the hypertensive effects of AIII.

On the other hand, there are no known side effects which result when renin is inhibited from acting on its substrate. Considerable research efforts have thus been carried out to develop useful inhibitors of renin. Past research efforts have been directed to renin antibodies, pepstatin, phospholipids and substrate analogs such as tetrapeptides and octapeptides to tridecapeptides. These inhibitors either demonstrate poor activity in inhibiting renin production or poor specificity for inhibiting renin only. However, Boger et al. have reported that statine-containing peptides possess potent and specific renin-inhibiting activity (*Nature*, Vol. 303, p. 81, 1983). In addition, Szelke and co-workers have described polypeptide analogs containing a non-peptide link (*Nature*, Vol. 299, p. 555, 1982) which also cause potent renin inhibition and show a high specificity for this enzyme.

DISCLOSURE OF THE INVENTION

In accordance with the present invention, there are renin inhibiting compounds of the formula

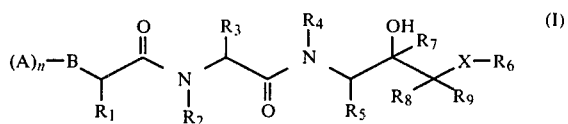

wherein A is an N-protecting group; n is 0 or 1; B is hydrogen, hydroxy, NH, loweralkyl or arylalkyl; with the proviso that when A is an N-protecting group, B is NH and when n is 0, B is hydrogen, hydroxy, loweralkyl or arylalkyl; $R_1$, $R_3$ and $R_5$ are loweralkyl or hydrophilic, lipophilic or aromatic amino acid side chains and may be the same or different; $R_2$, $R_4$, $R_7$, $R_8$ and $R_9$ are hydrogen or loweralkyl and may be the same or different; X is NH, O, S, SO or $SO_2$; and $R_6$ is loweralkyl, cycloalkyl, cycloalkylalkyl, aryl, arylalkyl or an N-protecting group, with the proviso that $R_6$ may be an N-protecting group when X is NH.

The preferable compounds are when $R_2$, $R_4$, $R_7$, $R_8$ and $R_9$ are hydrogen, $R_1$ is benzyl, α- or β-naphthylmethyl and $R_5$ is isobutyl and cyclohexylmethyl. The most preferable compounds are when $R_3$ is imidazole-4-yl-methyl, X is S, $SO_2$, or O and $R_5$ is cyclohexylmethyl.

The chiral centers of the compounds of the invention may have either the "R" or "S" configuration but preferably have an "S" configuration.

The term "N-protecting group" as used herein refers to those groups intended to protect the N-terminus against undesirable reactions during synthetic procedures or to prevent the attack of exopeptidases on the final compounds or to increase the solubility of the final compounds and includes but is not limited to sulfonyl, acyl, acetyl, pivaloyl, t-butylacetyl, t-butyloxycarbonyl(Boc), carbobenzyloxycarbonyl or benzoyl groups or an L- or D-aminoacyl residue, which may itself be N-protected similarly.

The term "loweralkyl" as used herein refers to straight or branched chain alkyl radicals containing from 1 to 6 carbon atoms including but not limited to methyl, ethyl, n-propyl, iso-propyl, n-butyl, iso-butyl, sec-butyl, 2-methylhexyl, n-pentyl, 1-methylbutyl, 2,2-dimethylbutyl, 2-methylpentyl, 2,2-dimethylpropyl, n-hexyl and the like.

The term "cycloalkyl" as used herein refers to an alicyclic residue containing 3-8 carbons and includes but is not limited to cyclohexyl and cyclopentyl.

The term "cycloalkylalkyl" as used herein refers to a cycloalkyl group as defined above appended to an alkyl radical of 1-4 carbons and includes but is not limited to cyclohexylmethyl and cyclopentylmethyl.

The term "aryl" as used herein refers to an phenyl or, naphthyl, unsubstituted or mono-substituted by halo or loweralkyl.

The term "arylalkyl" as used herein refers to a phenyl or naphthyl group as defined above appended to an alkyl radical of 1-4 carbons.

The terms "lipophilic or aromatic amino acid side chains" as used herein refers to those amino acid side chains which have the affinity for lipids or have an aromatic ring and include but are not limited to isobutyl, isopropyl, sec-butyl, benzyl, imidazole-4-yl-methyl, p-hydroxybenzyl, α- and β-naphthylmethyl, (pyrazolyl)methyl, (thiazoyl)methyl, and cyclohexylmethyl. The term "hydrophilic amino acid side chain" as used herein refers to those amino acid side chains which have an affinity for water and include but are not limited to, those of serine, threonine, allothreonine, homoserine, cysteine, ornithine, arginine, and glutamine. General reference to amino acid side chains in both the description and claims herein is to be taken as reference to such, whether naturally occurring in proteins or not, and to both D- and L-forms.

The terms "Ala", "His", "Leu" and "Phe" as used herein refer to alanine, histidine, leucine and phenylalanine.

The following examples will serve to further illustrate preparation of novel compounds of the present invention.

EXAMPLE 1

3-t-Butyloxycarbonylamino-5-methylhex-1-ene

To a stirred suspension of methyltriphenyl phosphonium bromide (10.97 g, 30.70 mmol) in anhydrous tetrahydrofuran (200 ml) at −78° C. (dry ice/acetone bath) under an argon atmosphere, was added n-butyl lithium (19.8 ml of a 1.55M hexane solution) dropwise over the course of 5 minutes. After 10 minutes, the −78° C. bath was replaced with a 0° C. bath for one-half hour, at which time the resulting orange solution was cooled again to −78° C. The solution was then added dropwise by cannula to a stirred −78° C. solution of Boc-leucinal (6.00 g, 27.91 mmol) in anhydrous tetrahydrofuran (30 ml) over the course of one-half hour. The mixture was then allowed to warm to room temperature during a 3 hour period after which water (150 ml) was added. Extraction with hexane (4×100 ml) provided a combined organic phase which was washed with brine (100 ml), dried (Na$_2$SO$_4$), and concentrated to give crude 3-t-butyloxycarbonylamino-5-methylhex-1-ene (6.5 g). Chromatography with ether/hexane (1/9) provided pure 3-t-butyloxycarbonyl-amino-5-methylhex-1-ene (3.71 g, 60%). Mass spectrum: EI, M$^+$−57=156; CI, (M+H)$^+$=214.

EXAMPLE 2

3-t-Butyloxycarbonylamino-5-methyl-1,2-oxohexane

To a stirred solution of 3-t-butyloxycarbonyl-amino-5-methylhex-1-ene (0.43 g, 2.0 mmol) in dichloromethane (20 ml) was added m-chloroperbenzoic acid (MCPBA, 1.51 g of 80% MCPBA, 7.0 mmol). After 68 hours the reaction mixture was cooled to 0° C., and 0° C. 10% Na$_2$SO$_3$ (5 ml) was added with stirring. After 15 minutes, the solid was filtered off and extracted with dichloromethane. The combined organic phase was washed sequentially with 0° C. 10% Na$_2$SO$_3$ (6 ml), saturated NaHCO$_3$ (2×6 ml), and water (5 ml). Drying (MgSO$_4$), filtering, and evaporating provided crude 3-t-butyloxycarbonylamino-5-methyl-1,2-oxohexane (0.42 g) which was chromatographed on 50 g of SiO$_2$ (hexane/ether, 3/1) to give pure 3-t-butyloxycarbonylamino-5-methyl-1,2-oxohexane (0.27 g, 59%). Mass spectrum: M$^+$=229.

EXAMPLE 3

3-t-Butyloxycarbonylamino-1-cyclohexylmercapto-2-hydroxy-5-methylhexane

To a stirred solution of 3-t-butyloxycarbonylamino-5-methyl-1,2-oxohexane (200 mg, 0.87 mmol) in methanol (8.7 ml) was added cyclohexyl mercaptan (102 mg, 0.87 mmol) and triethylamine (88 mg, 0.87 mmol). The resultant solution was refluxed for 2 hours and then evaporated to give a residue which was chromatographed on 15 g of 40 m SiO$_2$ (7/3, hexane/ether) to give 281 mg (94%) of 3-t-butyloxycarbonylamino-1-cyclohexylmercapto-2-hydroxy-5-methylhexane. Mass spectrum: M$^+$=345.

Analysis Calcd.: C, 62.6; H, 10.2; N, 4.0. Found: C, 62.9; H, 10.4; N, 3.9.

EXAMPLE 4

3-t-Butyloxycarbonylamino-2-hydroxy-5-methyl-1-(-phenylpropylmercapto)hexane

Using the procedure of Example 3, but replacing cyclohexyl mercaptan with 3-phenylpropyl mercaptan, gave the desired compound (93% yield). Mass spectrum: M$^+$=381.

Analysis Calcd: C, 66.1; H, 9.3; N, 3.7. Found: C, 66.3; N, 9.4; H, 3.6.

EXAMPLE 5

3-t-Butyloxycarbonylamino-2-hydroxy-5-methyl-1-phenylmercaptohexane

Using the procedure of Example 3, but replacing cyclohexyl mercaptan with phenyl mercaptan, gave the desired compound (93% yield). Mass Spectrum: M$^+$=339.

EXAMPLE 6

3-t-Butyloxycarbonylamino-2-hydroxy-5-methyl-1-β-naphthylmercaptohexane

Using the procedure of Example 3, but replacing cyclohexyl mercaptan with β-naphthyl mercaptan, gave the desired compound (65% yield). Mass spectrum: M$^+$=389.

EXAMPLE 7

1-Benzylmercapto-3-t-butyloxycarbonylamino-2-hydroxy-5-methylhexane

Using the procedure of Example 3, but replacing cyclohexyl mercaptan with benzyl mercaptan, gave the desired compound (57% yield). Mass spectrum: M$^+$=353.

EXAMPLE 8

1-p-Bromophenylmercapto-3-t-butyloxycarbonylamino-2-hydroxy-5-methylhexane

Using the procedure of Example 3, but replacing cyclohexyl mercaptan with p-bromophenyl mercaptan, gave the desired compound (71% yield). Mass spectrum: M$^+$=418.

EXAMPLE 9

3-t-Butyloxycarbonylamino-2-hydroxy-5-methyl-1-phenoxyhexane

To a stirred solution of 3-t-butyloxycarbonylamino-5-methyl-1,2-oxohexane (200 mg, 0.87 mmol) in methanol (8.7 ml) were added phenol (90 mg, 0.96 mmol) and triethylamine (97 mg, 0.96 mmol). The solution was refluxed for 44 hours and was then evaporated to give a residue which was chromatographed on 25 g of 40 m SiO$_2$ (7/3, hexane/ether) to give 71 mg (25%) of pure 3-t-butyloxycarbonylamino-2-hydroxy-5-methyl-1-phenoxyhexane. Mass spectrum: M+ =323.

EXAMPLE 10

3-t-Butyloxycarbonylamino-2-hydroxy-5-methyl-1-phenylaminohexane

To a stirred solution of 3-t-butyloxycarbonylamino-5-1,2-oxohexane (200 mg, 0.87 mmol) in methanol (10 ml) was added aniline (79 μl, 0.87 mmol). The solution was refluxed for approximately 20 hours and was then evaporated to give a residue which was chromatographed on SiO$_2$ (3/2, hexane/ether) to give 140 mg (50% of 3-t-butyloxycarbonylamino-2-hydroxy-5-methyl-1-phenylaminohexane). Mass spectrum: M+ =322.

EXAMPLE 11

3-Amino-1-cyclohexylmercapto-2-hydroxy-5-methylhexane hydrochloride

To a stirred solution of approximately 0.25 mmol of the resultant compound of Example 3 in methanol was added methanolic HCl (10 ml of approximately 0.75M). After 8-12 hours, the solvent was evaporated, and the desired compound was used without further purification.

EXAMPLE 12

3-Amino-2-hydroxy-5-methyl-1-(δ-phenylpropylmercapto)hexane hydrochloride

Using the procedure of Example 11 with the resultant compound of Example 4, gave the desired compound.

EXAMPLE 13

3-Amino-2-hydroxy-5-methyl-1-phenylmercaptohexane hydrochloride

Using the procedure of Example 11 with the resultant compound of Example 5, gave the desired compound.

EXAMPLE 14

3-Amino-2-hydroxy-5-methyl-1-β-naphthylmercaptohexane hydrochloride

Using the procedure of Example 11 with the resultant compound of Example 6, gave the desired compound.

EXAMPLE 15

3-Amino-1-benzylmercapto-2-hydroxy-5-methylhexane hydrochloride

Using the procedure of Example 11 with the resultant compound of Example 7, gave the desired compound.

Example 16

3-Amino-1-p-bromophenylmercapto-2-hydroxy-5-methylhexane hydrochloride

Using the procedure of Example 11 with the resultant compound of Example 8, gave the desired compound.

EXAMPLE 17

3-Amino-2-hydroxy-5-methyl-1-phenoxyhexane hydrochloride

Using the procedure of Example 11 with the resultant compound of Example 9, gave the desired compound.

EXAMPLE 18

3-Amino-2-hydroxy-5-methyl-1-phenylaminohexane hydrochloride

Using the procedure of Example 11 with the resultant compound of Example 10, gave the desired compound.

EXAMPLE 19

Boc-His Amide of 3-amino-1-cyclohexylmercapto-2-hydroxy-5-methylhexane

To a stirred suspension of Boc-His-OH (72 mg, 0.28 mmol) in dry dimethylformamide (3 ml) at −23° C. was added a solution of 3-amino-1-cyclohexylmercapto-2-hydroxy-5-methylhexane hydrochloride (derived from 98 mg, 0.28 mmol), of 3-t-butyloxycarbonylamino-1-cyclohexylmercapto-2-hydroxy-5-methylhexane using the procedure of Example 11) in dry dimethylformamide (2 ml) containing N-methylmorpholine (29 mg, 0.28 mmol). Hydroxybenzotriazole (HOBT, 58 mg, 0.43 mmol) and N,N'-dicyclohexylcarbodiimide (DCC, 59 mg, 0.28 mmol) were then added sequentially. After 2 hours the mixture was allowed to warm to room temperature. After 22 hours the mixture was filtered, evaporated, and partitioned between ethyl acetate (18 ml) and saturated NaHCO$_3$ (6 ml). The layers were separated, and the organic phase was washed with brine (5 ml), dried (Na$_2$SO$_4$), filtered, and evaporated to a solid which was chromatographed on SiO$_2$ (9/1, dichloromethane/methanol) to give 86 mg (63%) of the desired compound. Mass spectrum: (M+H)+ =483.

EXAMPLE 20

Boc-His Amide of 3-amino-2-hydroxy-5-methyl-1-(-phenylpropylmercapto)hexane

Following the procedure of Example 19 but using 3-amino-2-hydroxy-5-methyl-1-(-phenylpropylmercapto)hexane hydrochloride as opposed to 3-amino-1-cyclohexylmercapto-2-hydroxy-5-methylhexane hydrochloride, gave the desired compound in 62% yield. Mass spectrum: (M+H)+ =519.

EXAMPLE 21

Boc-Phe-His Amide of 3-amino-1-cyclohexylmercapto-2-hydroxy-5-methylhexane

The resultant compound of Example 19 was treated with methanolic HCl according to the procedure used in Examples 11-18, yielding the corresponding deprotected HCl salt which was used as described below without further purification.

To a stirred −12° C. solution of Boc-Phe-OH (19.2 mg, 0.0725 mmol) in anhydrous tetrahydrofuran (3 ml) was added N-methylmorpholine (8.0 1, 0.0725 mmol) in a dropwise fashion followed by isobutylchloroformate (9.4 1, 0.0725 mmol). After 3 minutes, a −12° C. solution of the above HCl salt in anhydrous tetrahydrofuran (2 ml) containing N-methylmorpholine (16.0 1, 0.145 mmol) was added over the course of 30 seconds. After 15 minutes, the mixture was allowed to warm to room temperature for 3 hours at which time the solvent was evaporated, and the residue was partitioned between ethyl acetate (20 ml) and saturated NaHCO$_3$ (6 ml). The layers were separated and the organic phase was washed with brine (5 ml). Drying (Na$_2$SO$_4$), evaporating, and chromatographing the resulting solid on SiO$_2$ (9/1, dichloromethane/methanol) provided 11 mg of the desired compound (24% yield). Mass spectrum: (M+H)$^+$ =630.

EXAMPLE 22

Boc-Phe-His amide of 3-amino-2-hydroxy-5-methyl-1-(-phenylpropylmercapto)hexane

Using the procedure of Example 21 with the resultant compound of Example 20, instead of Example 19, gave the desired compound (18% yield). Mass spectrum: (M+H)$^+$ =666.

EXAMPLE 23

Boc-Phe-His amide of 3-amino-2-hydroxy-5-methyl-1-phenylmercaptohexane

3-Amino-2-hydroxy-5-methyl-1-phenylmercaptohexane hydrochloride was prepared from 3-t-butyloxycarbonylamino-2-hydroxy-5-methyl-1-phenylmercaptohexane (0.610 mmol), using the procedure of Example 13, and was then partitioned between water (25 ml), brine (4 ml), and ether (10 ml). The layers were separated, and the aqueous phase was basified to pH 8 with 2M NaOH. Extraction with chloroform (4×7 ml), drying (Na$_2$SO$_4$), and evaporating provided 91 mg (62%) of the corresponding free base (M$^+$=239) which was used without further purification.

To a stirred −23° C. solution of Boc-Phe-His-OH (153 mg, 0.38 mmol) in anhydrous dimethylformamide (5 ml) was added a solution of the above free base in dimethylformamide. Hydroxybenzotriazole (HOBT) and dicyclohexyl carbodiimide (DCC) were then added sequentially. After 2.5 hours, the mixture was allowed to warm to room temperature for 16 hours, at which time the mixture was filtered and evaporated to a residue which was partitioned between ethyl acetate (20 ml) and saturated NaHCO$_3$ (8 ml). The organic phase was then washed separately with saturated NaHCO$_3$ (8 ml) and brine (8 ml). Drying (Na$_2$SO$_4$) and evaporating provided a white solid which was chromatographed on SiO$_2$ (95/5, dichloromethane/methanol) to give 180 mg (75%) of the desired compound. Mass spectrum: (M+H)$^+$ =624.

EXAMPLE 24

Boc-Phe-Ala amide of 3-amino-2-hydroxy-5-methyl-1-(δ-phenylpropylmercapto)hexane To a stirred −12° C. solution of Boc-Phe-Ala-OH (47.8 mg, 0.142 mmol) in anhydrous tetrahydrofuran (3 ml) were added N-methylmorpholine (15.6 μl, 0.142 mmol) and isobutylchloroformate (18.4 μl, 0.142 mmol) sequentially. After 3 minutes, a −12° C. solution of the resultant compound of Example 12 (0.142 mmol) in anhydrous tetrahydrofuran (2 ml) containing N-methylmorpholine (0.142 mmol) was added. Ten minutes later, the mixture was allowed to warm to room temperature for 2 hours, at which time the solvent was evaporated, and the resulting residue was partitioned between ethyl acetate (20 ml) and saturated NaHCO$_3$ (5 ml). The organic phase was washed sequentially with 0.01M H$_3$PO$_4$ (3 ml) and brine (5 ml). Drying (Na$_2$SO$_4$) and evaporating provided 79 mg (93%) of the desired compound. Mass spectrum: (M+H)$^+$ =600.

Analysis Calcd: C, 66.1; H, 8.2; N, 7.0. Found: C, 65.9; H, 8.4; N, 6.9.

EXAMPLE 25

Boc-Phe-Ala amide of 3-amino-2-hydroxy-5-methyl-1-phenylmercaptohexane

Using the procedure of Example 24 with the resultant compound of Example 13, gave the desired compound. Mass spectrum: (M+H)$^+$ =558.

Analysis Calcd for: C$_{30}$H$_{43}$N$_3$O$_5$S.H$_2$O: C, 62.6; H, 7.9; N, 7.3. Found: C, 62.6; H, 7.7; N, 7.0.

EXAMPLE 26

Boc-Phe-Ala amide of 3-amino-1-p-bromophenylmercapto-2-hydroxy-5-methylhexane

Using the procedure of Example 24 with the resultant compound of Example 16, gave the desired compound. NMR (300 MHz, CDCl$_3$, ppm): 0.9 (2d, 6H), 1.35 (d, 3H), 1.2–1.7 (m, 3H), 1.4 (s, 9H), 2.8–3.2 (m, 5H), 3.55–3.7 (m, 1H), 4.05 (m, 1H), 4.2–4.4 (m, 2H), 4.9 (d, 1H), 6.3–6.5 (2d, 2H), 7.15–7.45 (m, 9H).

EXAMPLE 27

Boc-Phe-Ala amide of 3-amino-2-hydroxy-5-methyl-1-β-naphthylmercaptohexane

Using the procedure of Example 24 with the resultant compound of Example 14, gave the desired compound. NMR (300 MHz, CDCl$_3$, ppm): 0.9 (d, 6H), 1.35 (d, 3H), 1.2–1.7 (m, 3H), 1.4 (s, 9H), 2.9–3.3 (m, 5H), 3.6–3.8 (m, 1H), 4.1 (m, 1H), 4.25–4.45 (m, 2H), 4.97 (d, 1H), 6.4 (d, 2H), 7.2 (m, 2H), 7.3 (m, 3H), 7.95 (m, 3H), 7.8 (m, 4H).

EXAMPLE 28

Boc-Phe-Ala amide of 3-amino-1-benzylmercapto-2-hydroxy-5-methylhexane

Using the procedure of Example 24 with the resultant compound of Example 15, gave the desired compound. Mass spectrum: (M+H)$^+$ =572.

Analysis Calcd. for: C$_{31}$H$_{45}$N$_3$O$_5$S.½H$_2$O: C, 64.1; H, 8.0; N, 7.2. Found: C, 64.1; H, 7.9; N, 7.5.

EXAMPLE 29

Boc-Phe-Ala amide of 3-amino-1-cyclohexyl mercapto-2-hydroxy-5-methylhexane

Using the same procedure of Example 24 with the resultant compound of Example 11, gave the desired compound. Mass spectrum: (M+H)$^+$ =564.

EXAMPLE 30

Boc-Phe-Ala amide of 3-amino-2-hydroxy-5-methyl-1-phenoxyhexane

Using the same procedure of Example 24 with the resultant compound of Example 17, gave the desired compound. Mass spectrum: (M+H)$^+$ =542.

Analysis Calcd. for: C$_{30}$H$_{43}$N$_3$O$_6$.½H$_2$O: C, 65.4; H, 8.0; N, 7.6. Found: C, 65.6; H, 8.1; N, 7.6.

EXAMPLE 31

Boc-Phe-Ala amide of 3-amino-2-hydroxy-5-methyl-1-phenylaminohexane

Using the same procedure of Example 24 with the resultant compound of Example 18 (which was a dihydrochloride) rather than Example 12, and utilizing two equivalents of N-methylmorpholine, rather than one, gave the desired compound. Mass spectrum: $(M+H)^+ = 541$.

Analysis Calcd. for: $C_{30}H_{44}N_4O_5 \cdot \frac{1}{2}H_2O$: C, 65.5; H, 8.2; N, 10.2. Found: C, 65.6; H, 8.1; N, 10.0.

EXAMPLE 32

Boc-Phe-Tyr amide of 3-amino-2-hydroxy-5-methyl-1-phenylmercaptohexane

Using the procedure of Example 25 with a stirred −12° C. solution of Boc-Phe-Tyr-OH rather than Boc-Phe-Ala-OH, gave the desired compound. NMR (300 MHz, CDCl$_3$, ppm): 0.9 (m, 6H), 1.2–1.5 (m, 3H), 1.35 (s, 9H), 2.5–3.3 (m, 6H), 3.4–3.6 (m, 1H), 4.0 (m, 1H), 4.25 (m, 1H), 4.55 (m, 1H), 4.9 (m, 1H), 5.6 (br s, 1H), 6.1–6.4 (br m, 2H), 6.7 (d, 2H), 6.9 (d, 2H), b 7.1–7.4 (m, 10H).

EXAMPLE 33

Boc-Phe-Phe amide of 3-amino-2-hydroxy-5-methyl-1-phenylmercaptohexane

Using the procedure of Example 25 with a stirred −12° C. solution of Boc-Phe-Phe-OH rather than Boc-Phe-Ala-OH, gave the desired compound. NMR (300 MHz, CDCl$_3$, ppm): 0.9 (2d, 6H), 1.2–1.7 (m, 3H), 1.3 (s, 9$_H$), 2.5–3.3 (m, 7H), 3.5 (m, 1H), 4.0 (m, 1H), 4.25 (m, 1H), 4.6 (m, 1H), 4.9 (br m, 1H), 6.2 (br d, 1H), 6.3 (br d, 1H), 7.0–7.4 (m, 15H).

EXAMPLE 34

2-t-Butyloxycarbonylamino-1-phenylbut-3-ene

Using the procedure of Example 1, but replacing Boc-leucinal with Boc-phenylalanal, gave the desired compound. Mass spectrum: $M^+ = 247$.

EXAMPLE 35

2-t-Butyloxycarbonylamino-1-cyclohexylbut-3-ene

Using the procedure of Example 1, but replacing Boc-leucinal with Boc-cyclohexylalanal, gave the desired compound. Mass spectrum: $(M+H)^+ = 254$.

EXAMPLE 36

3-t-Butyloxycarbonylamino-4-phenyl-1,2-oxobutane

Using the procedure of Example 2 with the resultant compound of Example 34, gave the desired compound. Mass spectrum: $(M+H)^+ = 264$.

EXAMPLE 37

3-t-Butyloxycarbonylamino-4-cyclohexyl-1,2-oxobutane

Using the procedure of Example 2 with the resultant compound of Example 35, gave the desired compound. Mass spectrum: $(M+H)^+ = 270$.

EXAMPLE 38

3-t-Butyloxycarbonylamino-1-cyclohexylmercapto-2-hydroxy-4-phenylbutane

Using the procedure of Example 3 with the resultant compound of Example 36, gave the desired compound. Mass spectrum: $(M+H)^+ = 380$.

EXAMPLE 39

3-t-Butyloxycarbonylamino-4-cyclohexyl-2-hydroxy-1-isopropylmercaptobutane

Using the procedure of Example 3 with the resultant compound of Example 37, but replacing cyclohexyl mercaptan with isopropyl mercaptan, gave the desired compound. Mass spectrum: $(M+H)^+ = 346$.

EXAMPLE 40

3-t-Butyloxycarbonylamino-4-cyclohexyl-1-cyclohexylmercapto-2-hydroxybutane

Using the procedure of Example 3 with the resultant compound of Example 37, gave the desired compound. Mass spectrum: $M^+ = 385$.

EXAMPLE 41

3-t-Butyloxycarbonylamino-4-cyclohexyl-1-cyclohexylsulfonyl-2-hydroxybutane

Treating the resultant compound of Example 40 with 2.5 equivalents of 3-chloroperoxybenzoic acid in dichloromethane, gave the desired compound after chromatography. Mass spectrum: $(M+H)^+ = 418$.

EXAMPLE 42

3-t-Butyloxycarbonylamino-1-cyclohexylsulfinyl-2-hydroxy-5-methylhexane

Treating the resultant compound of Example 3 with 1.05 equivalents of 3-chloroperoxybenzoic acid in dichloromethane, gave the desired compound after chromatography. Mass spectrum: $M^+ = 361$.

EXAMPLE 43

1-Allylmercapto-3-t-butyloxycarbonylamino-4-cyclohexyl-2-hydroxybutane

Using the procedure of Example 3 with the resultant compound of Example 37, but replacing cyclohexylmercaptan with allyl mercaptan, gave the desired compound.

EXAMPLE 44

3-Amino-1-cyclohexylmercapto-2-hydroxy-4-phenylbutanebutane hydrochloride

Using the procedure of Example 11 with the resultant compound of Example 38, gave the desired compound.

EXAMPLE 45

3-Amino-4-cyclohexyl-2-hydroxy-1-isopropylmercapto hydrochloride

Using the procedure of Example 11 with the resultant compound of Example 39, gave the desired compound.

EXAMPLE 46

3-Amino-4-cyclohexyl-1-cyclohexylmercapto-2-hydroxybutane hydrochloride

Using the procedure of Example 11 with the resultant compound of Example 40, gave the desired compound.

EXAMPLE 47

3-Amino-4-cyclohexyl-1-cyclohexylsulfonyl-2-hydroxybutane hydrochloride

Using the procedure of Example 11 with the resultant compound of Example 41, gave the desired compound.

EXAMPLE 48

3-Amino-1-cyclohexylsulfinyl-2-hydroxy-5-methylhexane hydrochloride

Using the procedure of Example 11 with the resultant compound of Example 42, gave the desired compound.

EXAMPLE 49

1-Allylmercapto-3-amino-4-cyclohexyl-2-hydroxybutane hydrochloride

Using the procedure of Example 11 with the resultant compound of Example 43, gave the desired compound.

EXAMPLE 50

Boc-Phe-His amide of 3-amino-1-cyclohexylmercapto-2hydroxy-4-phenylbutane

Using the procedure of Example 23 with the resultant compound of Example 44, but replacing the free base with the amine hydrochloride and one equivalent of N-methylmorpholine, gave the desired product. Mass spectrum: $(M+H)^+ = 664$.

EXAMPLE 51

Boc-Phe-His amide of 3-amino-4-cyclohexyl-2-hydroxy-1-isopropylmercaptobutane

Using the procedure of Example 50 with the resultant compound of Example 45 gave the desired compound. Mass spectrum: $(M+H)^+ = 630$.

EXAMPLE 52

Boc-Phe-His amide of 3-amino-4-cyclohexyl-1-cyclohexylmercapto-2-hydroxybutane

Using the procedure of Example 50 with the resultant compound of Example 46 gave the desired compound. Mass spectrum: $(M+H)^+ = 670$.

EXAMPLE 53

Boc-β-Hal-His amide of 3-amino-4-cyclohexyl-1-cyclohexylmercapto-2-hydroxybutane Using the procedure of Example 50 with the resultant compound of Example 46, but replacing Boc-Phe-His with Boc-β-Naphthylalanine-His, gave the desired compound. Mass spectrum: $(M+H)^+ = 720$.

EXAMPLE 54

Boc-Phe-His amide of 3-amino-4-cyclohexyl-1-cyclohexylsulfonyl-2-hydroxybutane

Using the procedure of Example 50 with the resultant compound of Example 47 gave the desired compound.

EXAMPLE 55

Boc-Phe-Ala amide of 3-amino-1-cyclohexylsulfinyl-2-hydroxy-5-methylhexane

Using the procedure of Example 24 with the resultant compound of Example 48, gave the desired compound. Mass spectrum: $M^+ = 579$.

EXAMPLE 56

Boc-Phe-Ala amide of 1-allylmercapto-3-amino-4-cyclohexyl-2-hydroxybutane

Using the procedure of Example 24 with the resultant compound of Example 49, gave the desired compound.

EXAMPLE 57

(S)-5-Methyl-3-[(toluenesulfonyl) amino]-2-hexanone

To a stirred −78° C. solution of tosyl-Leu (Ts-Leu, 3.00 g, 10.5 mmol) in dry tetrahydrofuran (THF, 60 ml) was added 23.0 ml of a 1.39M methyl lithium solution in ether. The mixture was warmed to room temperature for 1 hour and then poured into 55 ml of 0° C. 1M HCl. Extracting with ether, washing the combining combined extracts with saturated NaHCO$_3$ and brine, drying, and evaporating gave 2.39 g (80%) of the desired compound. Mass spectrum: $(M+H)^+ = 284$.

EXAMPLE 58

1-t-Butyloxy-2,5-dimethyl-2-hydroxy-3-(toluenesulfonyl) aminohexane

To a −78° C. solution of the resultant compound of Example 57 (1.0 g, 3.5 mmol) in dry THF (7 ml) was added 3 equivalent, of t-butoxymethyl lithium [E. J. Corey and T. M. Eckridge, Tetrahedron Letters, 3165 (1983)]. The mixture was warmed to room temperature for 4 hours and then poured into water. Acidification with 0.1M H$_3$PO$_4$, extraction into ether, washing with brine, drying, and evaporating gave 1.1 g, (85%) of the desired compound. Mass spectrum: $M^+ = 371$.

EXAMPLE 59

3-Amino-1-t-butyloxy-2,5-dimethyl-2-hydroxyhexane

To a solution of the resultant compound of Example 58 (0.40 g, 1.1 mmol) in liquid NH$_3$ (80 ml) was added sodium (0.25 g, 11 mmol) with stirring. After 5 hours the solvent was evaporated and the residue was partitioned between benzene (40 ml), ethanol (10 ml), and water (30 ml). The layers were separated and the aqueous phase was extracted with ether. The combined organic layers were dried and evaporated to give 0.19 g (79%) of the desired compound. Mass spectrum: $M^+ = 217$.

EXAMPLE 60

Boc-Phe-His amide of 3-amino-1-t-butyloxy-2,5-dimethyl-2-hydroxyhexane

Using the procedure of Example 23 with the resultant compound of Example 59, gave the desired product.

EXAMPLE 6

4-t-Butyloxyamino-2,6-dimethylhept-2-ene

Using the procedure of Example 1, but replacing methyltriphenylphosphonium bromide with isopropyltriphenylphosphonium bromide, gave the desired compound.

EXAMPLE 62

4-Amino-2,6-dimethylhept-2-ene hydrochloride

Using the procedure of Example 11 with the resultant compound of Example 61, gave the desired compound.

EXAMPLE 63

Boc-Phe-Ala amide of 4-amino-2,6-dimethylhept-2-ene

Using the procedure of Example 24 with the resultant compound of Example 62, gave the desired compound.

EXAMPLE 64

Boc-Phe-Ala amide of 4-amino-2,6-dimethyl 2,3-oxoheptane

Using the procedure of Example 2 with the resultant compound of Example 63, gave the desired compound.

EXAMPLE 65

Boc-Phe-Ala amide of 4-amino-2,6-dimethyl-2-isobutylmercapto-3-hydroxyheptane

Using the procedure of Example 3 with the resultant compound of Example 64, but replacing cyclohexylmercaptan with isobutylmercaptan, gave the desired compound.

EXAMPLE 66

4-Cyclohexyl-1-cyclohexymercapto-2-hydroxy-3-(methylamino)butane

To a stirred suspension of lithium aluminum hydride (LAH, 4 mmol) in THF (15 ml) was added a solution of the resultant compound of Example 40 (1 mmol). The mixture was refluxed overnight, cooled, quenched sequentially with water (0.16 ml) and 3M NaOH (0.50 ml), filtered, dried, and evaporated to give the desired compound in 59% yield.

EXAMPLE 67

Boc-Phe-His amide of 4-cyclohexyl-1-cyclohexylmercapto-2-hydroxy-3-(methylamino)butane Using the procedure of Example 23 with the resultant compound of Example 66, gave the desired product.

EXAMPLE 68

N,N (α, α)-Methyl, t-Butyloxycarbonyl-N(π)-benzyloxymethyl-L-histidine

N(α)-t-Butyloxycarbonyl-N(π)-benzyloxymethyl-L-histidine [T. Brown, J. H. Jones, J. D. Richards, J. Chem. Soc., Perkin Trans. I, 1553 (1982)] was methylated according to a general procedure described in J. R. McDermott and N. L. Benoiton, Can. J. Chem., 1915 (1973), to give the desired product.

EXAMPLE 69

N,N(α, α)-Methyl-t-butyloxycarbonyl-N(π)-benzyloxymethyl-L-histidine Amide of 3-Amino-4-cyclohexyl-1-cyclohexylmercapto-2-hydroxybutane Using the procedure of Example 19 with the resultant compound of Example 46, but replacing Boc-His with the resultant compound of Example 68, gave the desired compound.

EXAMPLE 70

N(α)-Methyl-L-histidine amide of 3-amino-4-cyclohexyl-1-cyclohexylmercapto-2-hydroxybutane dihydrochloride salt The resultant compound of Example 69 (100 mg) was dissolved in 1M anhydrous HCl in anhydrous methanol and was hydrogenated at 3 atmospheres H$_2$ with 30 mg of Pd black for 8 h. Filtration and evaporation provided the desired compound (56 mg) which was used without further purification.

EXAMPLE 71

Boc-Phe-N(α)-methyl-L-histidine amide of 3-amino-4-cyclohexyl-1-cyclohexylmercapto-2-hydroxybutane Using the procedure of Example 21 with the resultant compound of Example 70 and two equivalents of N-methylmorpholine, gave the desired compound.

EXAMPLE 72

3-t-Butyloxycarbonylamino-4-cyclohexyl-1-cyclohexylmethylmercapto-2-hydroxybutane Using the procedure of Example 3 with the resultant compound of Example 37, but changing cyclohexyl mercaptan to cyclohexylmethyl mercaptan, gave the desired compound in 84% yield.

EXAMPLE 73

3-Amino-4-cyclohexyl-1-cyclohexylmethylmercapto-2-hydroxybutane hydrochloride

Using the procedure of Example 11 with the resultant compound of Example 72, gave the desired compound.

EXAMPLE 74

Boc-Phe-His amide of 3-amino-4-cyclohexyl-1-cyclohexylmethylmercapto-2-hydroxybutane Using the procedure of Example 50 with the resultant compound of Example 73, gave the desired compound.

EXAMPLE 75

1-Azido-3-t-butyloxyxcarbonylamino-2-hydroxy-5-methylhexane

A stirred solution of the resultant compound of Example 2 (1.0 mmol) in methanol (10 ml) was refluxed with sodium azide (2.4 mmol) and ammonium chloride (1.8 mmol) for 2 hours. The solvent was evaporated, and the residue was extracted with several portions of hot chloroform. The extract was filtered and evaporated to a residue which was chromatographed on SiO$_2$ eluting with hexane/ether mixtures to give the desired compound in 76% yield, mp=50°-52° C.

EXAMPLE 76

1-Amino-3-t-butyloxycarbonylamino-2-hydroxy-5-methylhexane Hydrochloride

The resultant compound of Example 75 (400 mg) dissolved in methanol containing added CHCl$_3$ was hydrogenated over 10% Pd/C (40 mg) with 3 atmospheres hydrogen. Filtration and evaporation gave the desired compound (305 mg).

EXAMPLE 77

3-t-Butyloxycarbonylamino-2-hydroxy-1-(isovalerylamino)-5-methylhexane

To a solution of the resultant compound of Example 76 (1.0 mmol) and triethyl amine (2.0 mmol) in chloroform (10 ml) cooled to 0° C. was added isovaleryl chloride (1.0 mmol) in CHCl$_3$ (2 ml). After 3 h, the solution was washed sequentially with 10% citric acid, saturated NaHCO$_3$, and brine. Drying and evaporating provided the desired compound.

EXAMPLE 78

3-Amino-2-hydroxyi-1-(isovalerylamino)-5-methylhexane Hydrochloride

Using the procedure of Example 11 with the resultant compound of Example 77, gave the desired compound.

EXAMPLE 79

Boc-Phe-His Amide of 3-Amino-2-hydroxy-1-(isovalerylamino)-5-methylhexane

Using the procedure of Example 50 with the resultant compound of Example 78, gave the desired compound.

EXAMPLE 80

Boc-His Amide of 3-Amino-4-cyclohexyl-1-cyclohexylmercapto-2-hydroxybutane

Using the procedure of Example 19 employing the resultant compound of Example 46, gave the desired compound. Mass spectrum: (M+H)$^+$ = 523.

Anal. calcd. for C$_{27}$H$_{46}$N$_4$O$_4$S: C, 62.04; H, 8.87; N, 10.72. Found: C, 61.72; H, 9.26; N, 10.59.

EXAMPLE 81

Dba-His Amide of 3-amino-4-cyclohexyl-1-cyclohexylmercapto-2-hydroxybutane

The compound of Example 80 was deprotected according to the method of Example 11. A solution of this material in dry dimethylformamide containing 1 equivalent of N-methylmorpholine was coupled to 2,2-dibenzylacetic acid (Dba-OH) using the procedure of Example 23, to give the desired compound. Mass spectrum: M$^+$ = 644.

EXAMPLE 82

Tba-Phe-His Amide of 3-amino-4-cyclohexyl-1-cyclohexylmercapto-2-hydroxybutane

Using the procedure of Example 81 and employing t-butylacetyl-Phe (Tba-Phe) in lieu of DbaOH provided the desired compound. Mass spectrum: (M+H)$^+$ = 668.

EXAMPLE 83

3-t-Butyloxycarbonylamino-4-cyclohexyl-2-hydroxy-1-isopropylsulfonylbutane

Using the procedure of Example 41 employing the resultant compound of Example 39, provided the desired compound. Mass spectrum: (M+H)$^+$ = 378.

Anal. calcd. for C$_{18}$H$_{35}$NO$_5$S: C, 57.26; H, 9.34; N, 3.71. Found: C, 57.13; H, 9.57; N, 3.60.

EXAMPLE 84

Boc-His Amide of 3-amino-4-cyclohexyl-2-hydroxy-1-isopropylsulfonylbutane

Using the procedure of Example 19 employing the resultant compound of Example 83, provided the desired compound. Mass spectrum: M$^+$ = 514.

EXAMPLE 85

Tba-Phe-His Amide of 3-amino-4-cyclohexyl--hydroxy-1-isopropylsulfonylbutane

Following the procedure of Example 82 and employing the resultant compound of Example 84 in lieu of the Boc His Amide of 3-amino-4-cyclohexyl-1-cyclohexylmercapto-2-hydrobutane provided the desired compound. Mass spectrum: (M+H)$^+$ = 660.

Anal. calcd. for C$_{36}$H$_{55}$N$_7$S.½H$_2$O): C, 60.82; H, 7.94; N, 9.85. Found: C, 60.70; H, 8.21; N, 9.63.

EXAMPLE 86

Dba-His Amide of 3-amino-4-cyclohexyl-2-hydroxy-1-isopropylsulfonylbutane

Using the procedure of Example 81 employing the resultant compound of Example 84, provided the desired compound. Mass spectrum: (M+H)$^+$ = 637.

EXAMPLE 87

Pp-His amide of 3-amino-4-cyclohexyl-1-cyclohexylmercapto-2-hydroxybutane

Using the procedure of Example 81, but replacing 2,2-dibenzylacetic acid with 3-phenylpropionic acid (Pp-OH), gave the desired compound.

EXAMPLE 88

Pl-His amide of 3-amino-4-cyclohexyl-1-cyclohexylmercapto-2-hydroxybutane

Using the procedure of Example 81, but replacing 2,2-dibenzylacetic acid with L-3-phenyllactic acid (Pl-OH), gave the desired compound.

EXAMPLE 89

Mpp-His amide of 3-amino-4-cyclohexyl-1-cyclohexylmercapto-2-hydroxybutane

Using the procedure of Example 81, but replacing 2,2-dibenzylacetic acid with 2(S)-methyl-3-phenylpropionic acid (Mpp-OH), gave the desired compound.

EXAMPLE 90

Boc-Ser amide of 3-amino-4-cyclohexyl-2-hydroxy-1-isopropylsulfonylbutane

The resultant compound of Example 83 was treated with methanolic HCl according to Example 11 to provide the corresponding deprotected HCl salt which was used as described below without further purification.

To a stirred −23° solution of Boc-Ser-OH (60 mg, 0.0291 mmol) in freshly dried dichloromethane (1 ml) were added sequentially N-methylmorpholine (33 ul, 0.0291 mmol) and isobutylchloroformate (38 ul, 0.0305 mmol).

After 5 minutes hydroxybenzotriazole (107 mg, 0.0795 mmol) was added in a single portion and the reaction stirred 15 minutes at 0° C. and cooled again to −23° C. The above HCl salt and N-methylmorpholine (33 ul, 0.0305 mmol) were added as a suspension in dichloromethane (1 ml). The reaction was stirred 1 hour at −23° C., 2 hours at room temperature, and partitioned between ethyl acetate and saturated NaHCO$_3$. The layers were separated and the organic phase washed sequentially with 10% HCl and brine, dried (Na$_2$SO$_4$) and concentrated in vacuo. The resulting film was chromatographed to provide 32 mg (26% yield) of the title compound. Mass spectrum: (M+H)$^+$=465.

EXAMPLE 91

Boc-Phe-Ser-amide of 3-amino-4-cyclohexyl-2-hydroxy-1-isopropylsulfonyl-butane

Following the procedure of Example 21 and employing the deprotected HCl salt of Example 90 provided the title compound. Mass spectrum: M$^+$=611.

Anal. calcd. for C$_{30}$H$_{49}$N$_3$O$_8$S: C,58.90; H, 8.07; N, 6.87 Found: C,58.86; H, 8.34; N,6.53.

The compounds of the present invention can be used in the form of salts derived from inorganic or organic acids. Included among such salts are the following: acetate, adipate, alginate, aspartate, benzoate, benzenesulfonate, bisulfate, butyrate, citrated, camphorate, camphorsulfonate, cyclopentanepropionate, digluconate, dodecylsulfate, ethanesulfonate, fumarate, glucoheptanoate, glycerophosphate, hemisulfate, heptonate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate. Also, the basic nitrogen-containing groups can be quarternized with such agents as loweralkyl halides, such as methyl, ethyl, propyl and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others. Water or oil-soluble or dispersible products are thereby obtained.

The novel compounds of the present invention possess an excellent degree of activity and specificity in treating renin-associated hypertension in a host. The ability of the compounds of the invention to inhibit human renal renin can be demonstrated in vitro by reacting a selected compound at varied concentrations with human renal renin, free from acid proteolytic activity, and with human renin substrate (angiotensinogen) at 37° C. and pH 6.0. At the end of the incubation, the amount of angiotensin I formed is measured by radioimmunoassay and the percent inhibition or renin is calculated. When tested in accordance with the foregoing procedure, the compounds of the invention demonstrated a high level of enzyme inhibition as shown on Table I.

Total daily dose administered to a host in single or divided doses may be in amounts, for example, from 0.001 to 10 mg/kg body weight daily and more usually 0.01 to 1 mg. Dosage unit compositions may contain such amounts or submultiples thereof to make up the daily dose.

The amount of active ingredient that may be combined with the carrier materials to produce a single dosage form will vary depending upon the host treated and the particular mode of administration.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The compounds of the present invention may be adminstered orally, parenterally, by inhalation spray, rectally or topically in dosage unit formulations containing conventional nontoxic pharmaceutically acceptable carriers, adjuvants and vehicles as desired. The term parenteral as used herein includes subcutaneous injections, intravenous, intramuscular, intrasternal injection or infusion techniques.

Injectable prepartion, for example, sterile injectable aqueous or oleagenous suspensions may be formulated according to the known art using suitable dispersing or wetting agents and suspending agents. The sterile injectable preparation may also be a sterile injectable solution or solution in a nontoxic parenterally acceptable diluent or solvent, for example, as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectibles.

Suppositories for rectal administration of the drug can be prepared by mixing the drug with a suitable nonirritating excipient such as cocoa butter and polyethylene glycols which are solid at ordinary temperatures but liquid at the rectal temperature and will therefor melt in the rectum and release the drug.

Solid dosage forms for oral administration may include capsules, tablets, pills, powders and granules. In such solid dosage forms, the active compound may be admixed with at least one inert diluent such as sucrose, lactose or starch. Such dosage forms may also comprise, as is normal practice, additional substances other than inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration may include pharmaceutically acceptable emulsions, solutions, suspensions, syrups and elixirs containing inert diluents commonly used in the art, such as water. Such compositions may also comprise adjuvants, such as wetting agents, emulsifying and suspending agents, and sweetening, flavoring and perfuming agents.

The foregoing is merely illustrative of the invention and is not intended to limit the invention to the disclosed compounds. Variations and changes which are obvious to one skilled in the art are intended to be within the scope and nature of the invention which are defined in the appended claims.

TABLE I

| Compounds (Example No.) | Inhibition |
|---|---|
| Example 23 | 56% @ $10^{-6}$ |
| Example 25 | 56% @ $10^{-5}$ |
| Example 28 | 57% @ $10^{-5}$ |
| Example 29 | 94% @ $10^{-5}$ |
| Example 31 | 31% @ $10^{-5}$ |
| Example 50 | 89% @ $10^{-7}$ |
| Example 51 | 80% @ $10^{-8}$ |
| Example 54 | 81% @ $10^{-8}$ |
| Example 55 | 46% @ $10^{-5}$ |
| Example 79 | 63% @ $10^{-6}$ |
| Example 81 | 71% @ $10^{-7}$ |
| Example 82 | 82% @ $10^{-8}$ |

We claim:

1. A renin inhibiting compound of the formula:

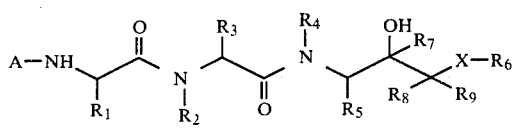

wherein A is a N-protecting group; $R_1$ is arylalkyl; $R_3$ is loweralkyl, arylalkyl, hydroxyloweralkyl, hydroxyarylalkyl, or imidazole-4-yl-loweralkyl; $R_5$ is loweralkyl, arylalkyl or cycloalkylalkyl; $R_2$, $R_4$, $R_7$, $R_8$ and $R_9$ are independently selected from hydrogen and loweralkyl; X is NH, O, S, SO or $SO_2$; and $R_6$ is loweralkyl, cycloalkyl, cycloalkylalkyl, aryl, arylalkyl or an N-protecting group when X is NH.

2. The renin inhibiting compounds of claim 1 wherein $R_2$, $R_4$, $R_7$, $R_8$ and $R_9$ are hydrogen.

3. The renin inhibiting compound of claim 2 wherein A is Boc, $R_1$ is benzyl, $R_3$ is methyl, $R_5$ is isobutyl, X is SO and $R_6$ is cyclohexyl.

4. The renin inhibiting compounds of claim 2 wherein $R_1$ is benzyl or α- or β-naphthyl.

5. The renin inhibiting compounds of claim 4 wherein $R_3$ is methyl.

6. The renin inhibiting compounds of claim 4 wherein $R_3$ is imidazole-4-yl-methyl.

7. The renin inhibiting comounds of claim 4 wherein $R_5$ is isobutyl.

8. The renin inhibiting compounds of claim 4 wherein $R_5$ is cyclohexylmethyl.

9. The renin inhibiting compounds of claim 4 wherein X is S or $SO_2$.

10. The renin inhibiting compounds of claim 4 wherein $R_6$ is cyclohexyl or isopropyl.

11. The renin inhibiting compounds of claim 4 wherein X is oxygen.

12. The renin inhibiting compounds of claim 4 wherein X is NH.

13. The renin inhibiting compounds of claim 2 wherein X is S, $R_1$ is benzyl, $R_3$ is imidazole-4-yl-methyl, $R_5$ is cyclohexylmethyl or benzyl and $R_6$ is isopropyl or cyclohexyl.

14. The renin inhibiting compounds of claim 2 wherein X is S, $R_1$ is β-naphthyl, $R_3$ is imidazole-4-yl-methyl, $R_5$ is cyclohexylmethyl, benzyl, or isobutyl and $R_6$ is cyclohexyl.

15. The renin inhibiting compounds of claim 2 wherein X is $SO_2$, $R_1$ is benzyl, $R_3$ is imidazole-4-yl-methyl, $R_5$ is cyclohexylmethyl and $R_6$ is cyclohexyl or isopropyl.

* * * * *